United States Patent [19]
O'Neal et al.

[11] Patent Number: 5,512,038
[45] Date of Patent: Apr. 30, 1996

[54] SPINAL RETRACTOR APPARATUS HAVING A CURVED BLADE

[76] Inventors: Darrell D. O'Neal, 500 Northside Cir., Suite R-3, Atlanta, Ga. 30309; Robert J. Schiess, III, 5580 Benton Woods Dr., Atlanta, Ga. 30342

[21] Appl. No.: 152,588

[22] Filed: Nov. 15, 1993

Related U.S. Application Data

[63] Continuation-in-part of Ser. No. 9,100, Jun. 4, 1993, Pat. No. Des. 353,887.

[51] Int. Cl.$^6$ ............................................. A61B 17/02
[52] U.S. Cl. ............................................. 600/210; 600/235
[58] Field of Search ................................ 128/20; 600/210, 600/215, 216, 225, 235

[56] References Cited

U.S. PATENT DOCUMENTS

| | | | |
|---|---|---|---|
| 4,151,837 | 5/1979 | Millard, Jr. et al. | 128/20 X |
| 4,412,532 | 11/1983 | Anthony | 128/20 |
| 4,610,243 | 9/1986 | Ray . | |
| 4,616,634 | 10/1986 | Vargas Garcia | 128/20 |
| 4,747,394 | 5/1988 | Watanabe . | |
| 4,747,395 | 5/1988 | Brief | 128/20 |
| 4,852,552 | 8/1989 | Chaux | 128/20 |
| 4,932,395 | 6/1990 | Mehdizadeh . | |
| 5,026,376 | 6/1991 | Greenberg . | |
| 5,052,373 | 10/1991 | Michelson . | |

FOREIGN PATENT DOCUMENTS

| | | | |
|---|---|---|---|
| 993416 | 10/1951 | France | 128/20 |
| 2302078 | 10/1976 | France | 128/20 |
| 3834358 | 4/1990 | Germany | 128/20 |
| 1482675 | 5/1989 | U.S.S.R. | 128/20 |

OTHER PUBLICATIONS

Undated brochure by Watanabe Orthopedic Systems, Inc.
Undated technique manual by AcroMed Spinal Retractor

*Primary Examiner*—Richard J. Apley
*Assistant Examiner*—John P. Leubecker
*Attorney, Agent, or Firm*—Bernstein & Associates

[57] ABSTRACT

Surgical retraction apparatus having a retractor blade with a curved blade and a quick release mechanism. The blade has a complex curved shape and notches on the sides to reduce tissue damage during retraction. Blades can be removed from a rack and pinion mechanism by sliding the bushing of the blade over the rack arm.

1 Claim, 6 Drawing Sheets

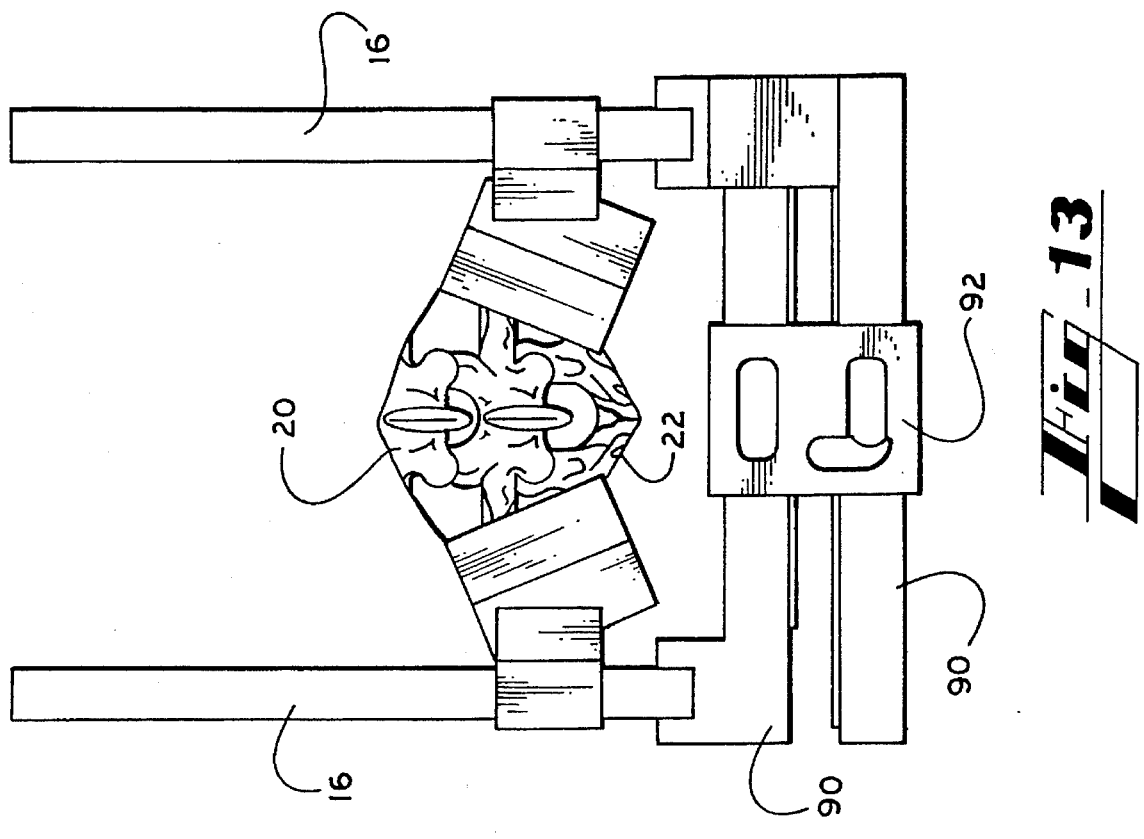
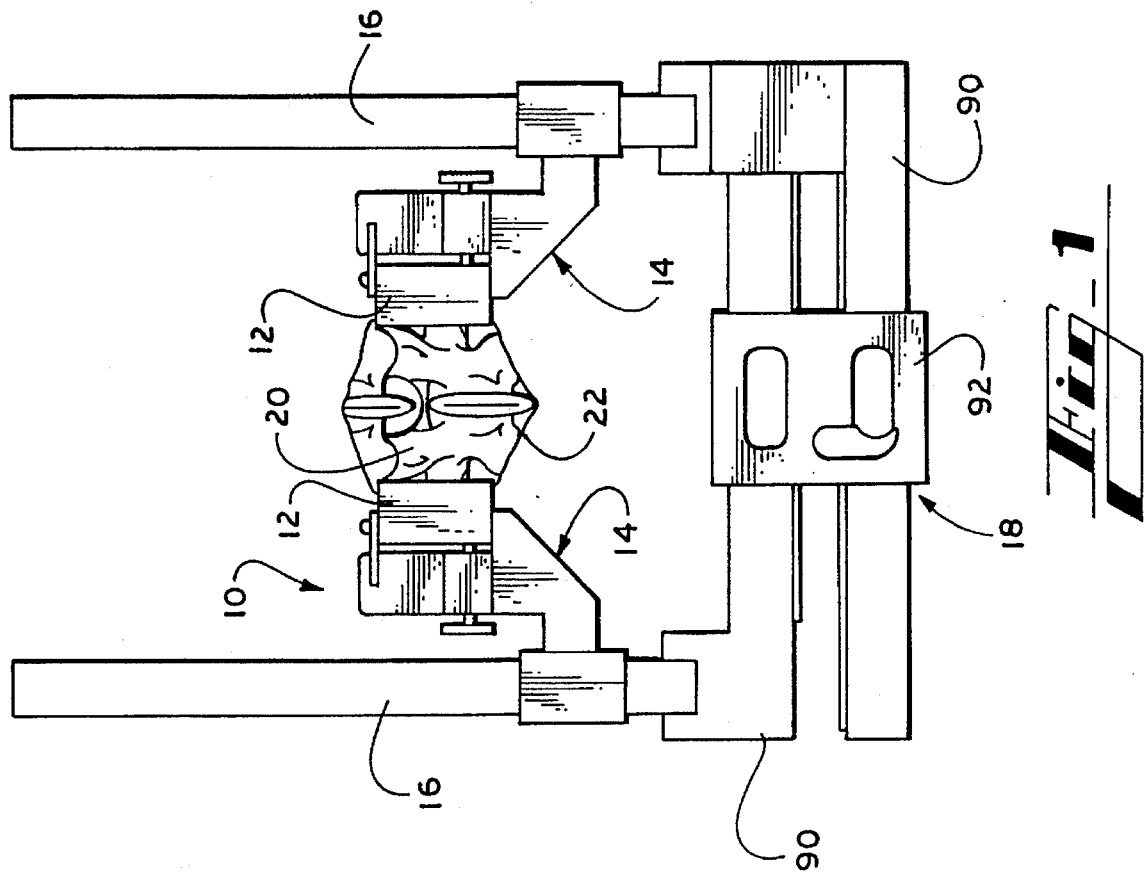

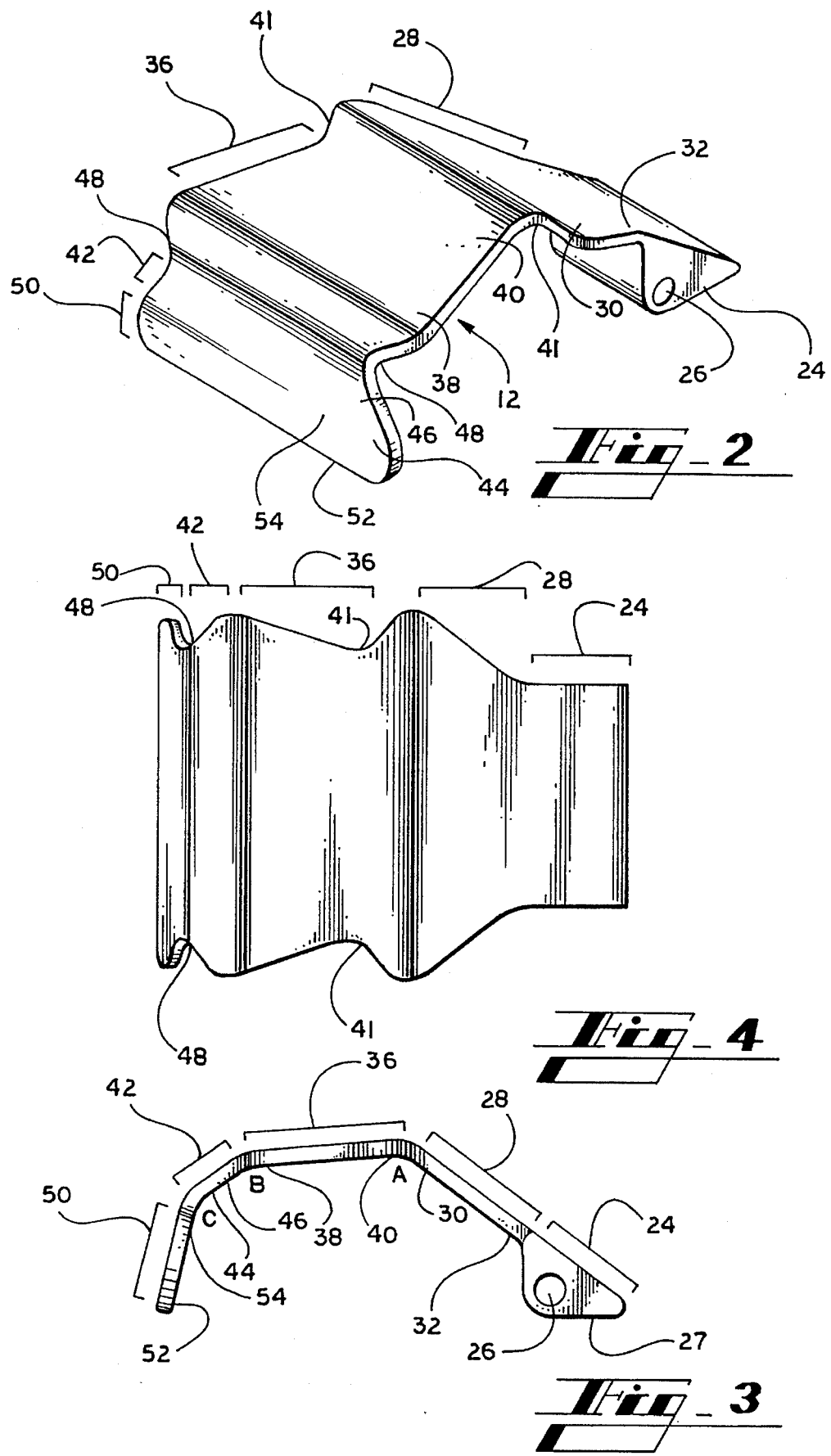

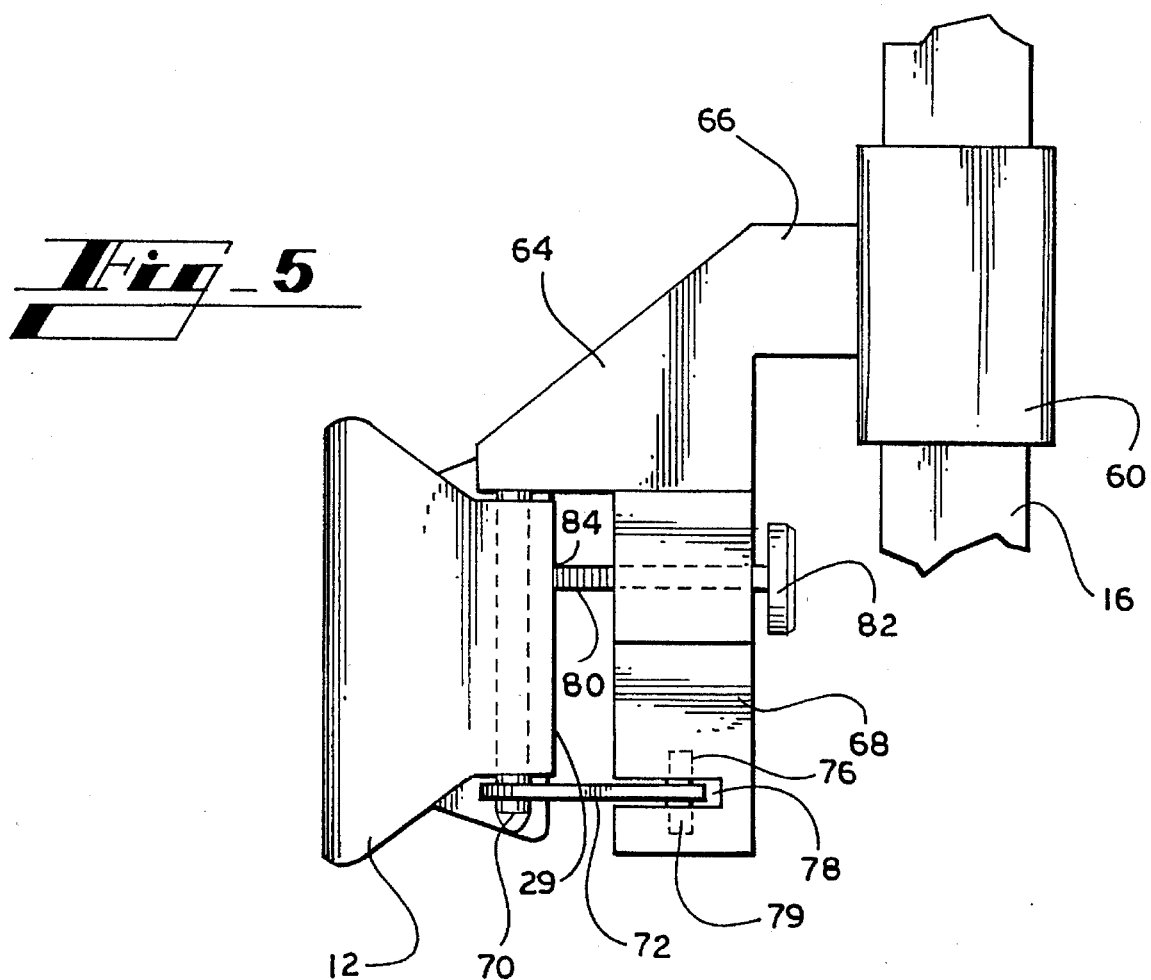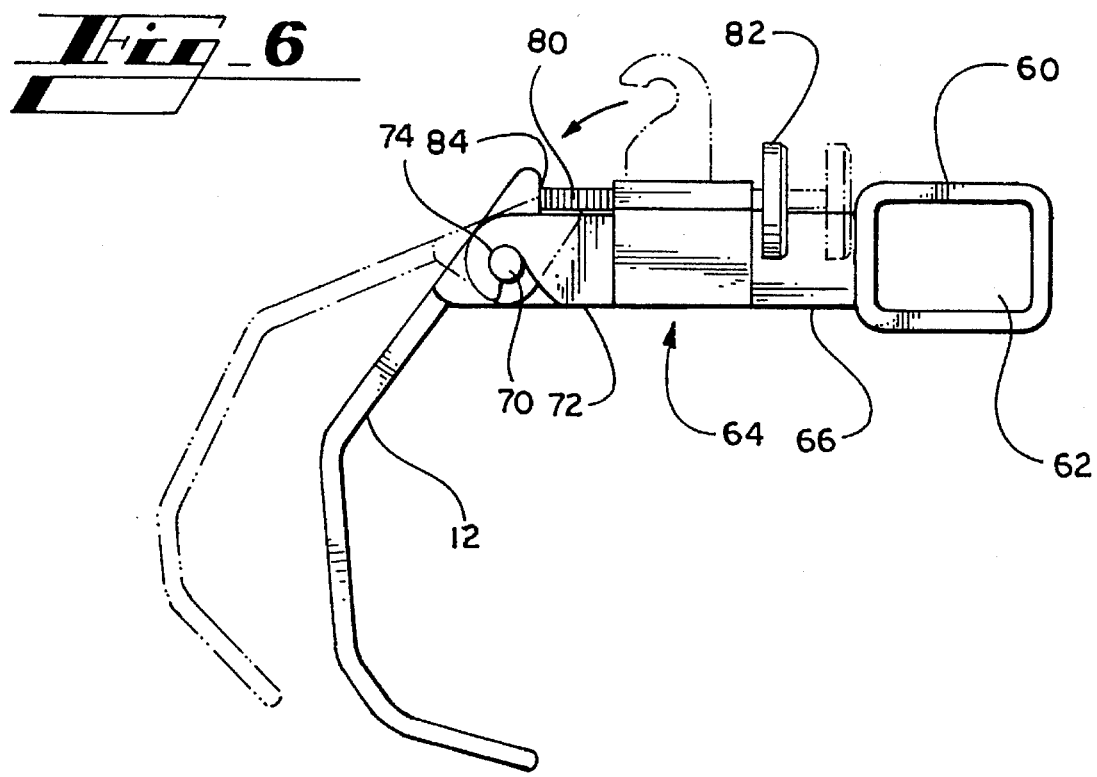

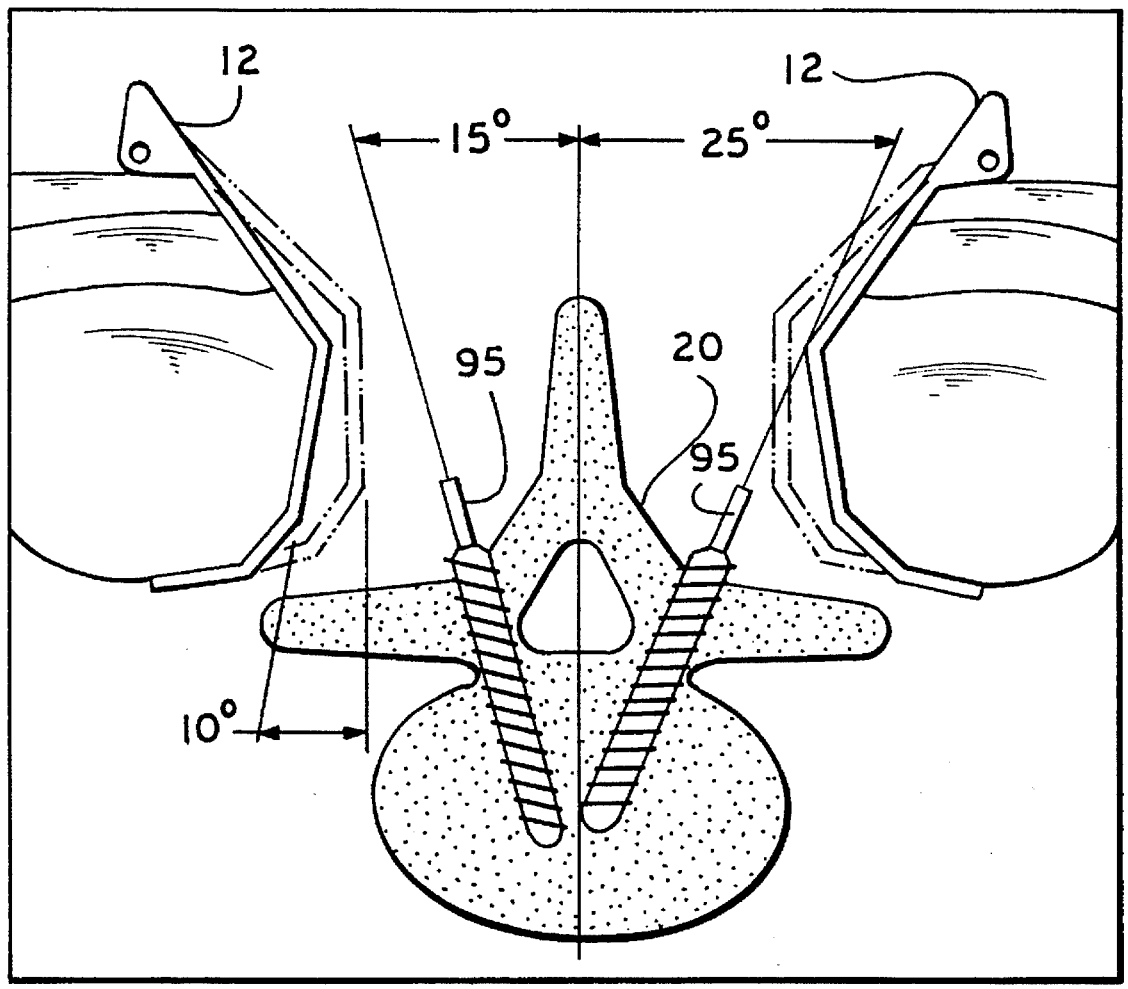
Fig_7

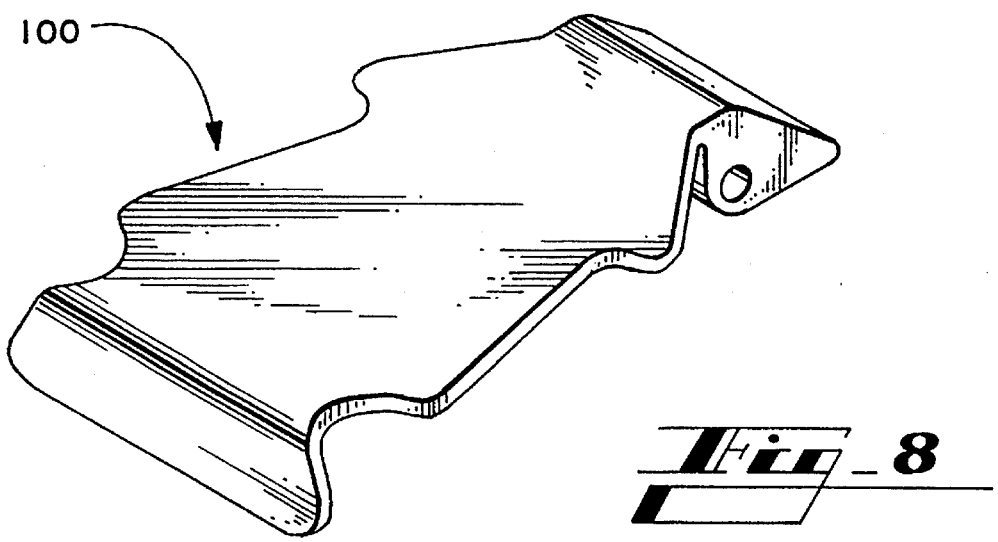
Fig_8
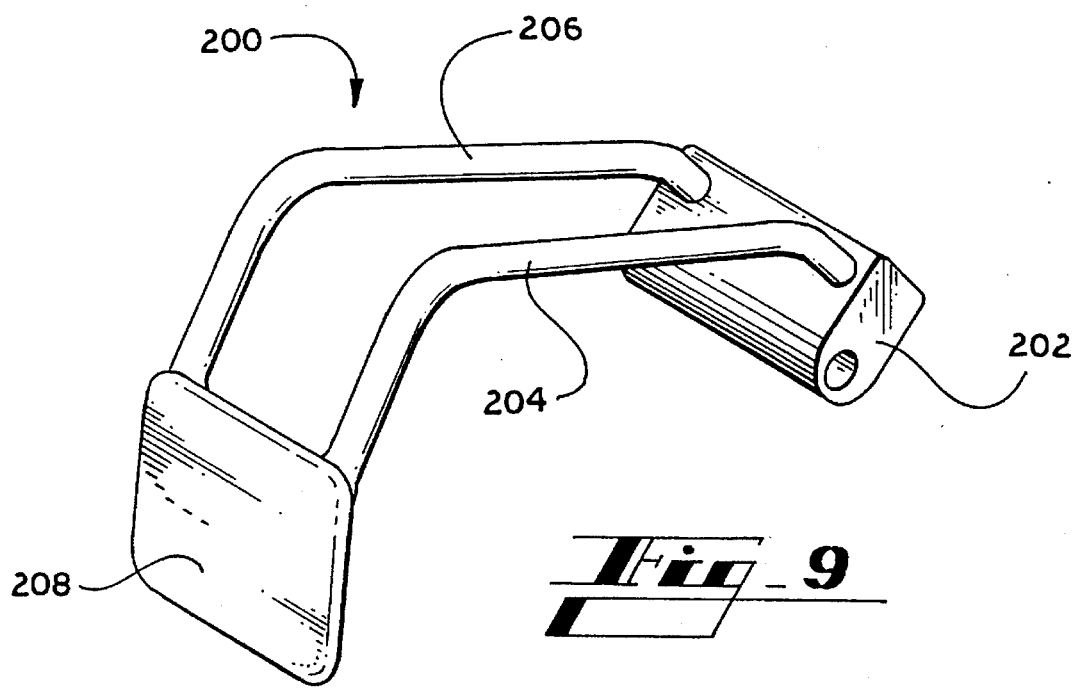
Fig_9

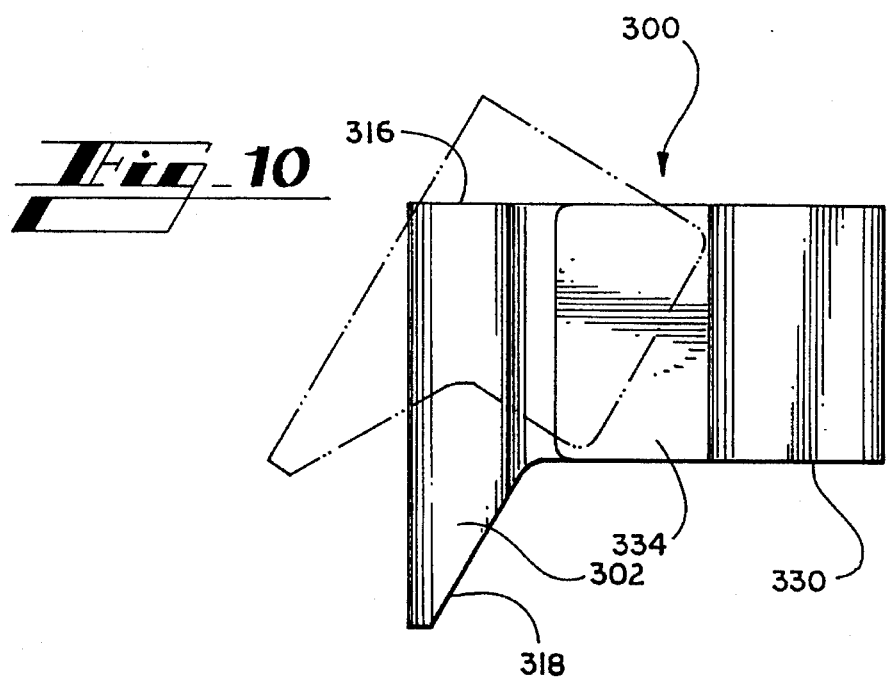
_Fig_10
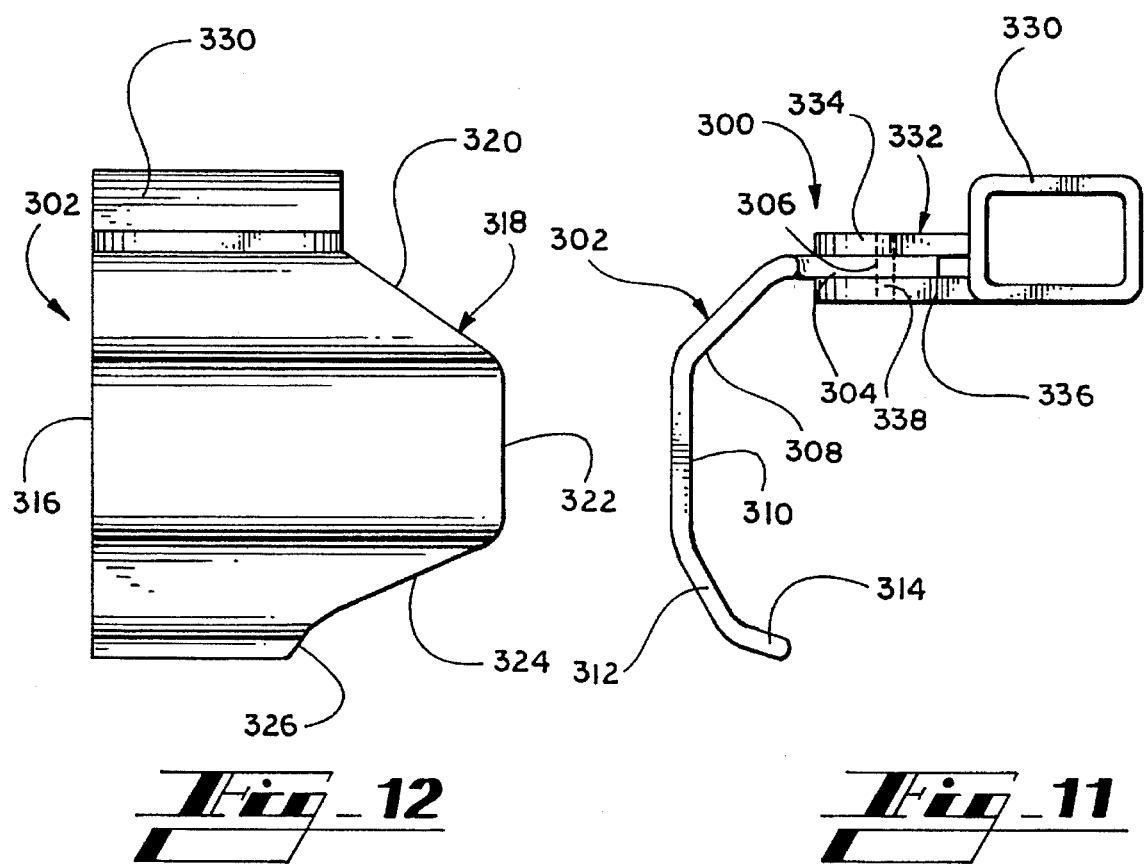
_Fig_12
_Fig_11
SPINAL RETRACTOR APPARATUS HAVING A CURVED BLADE

CROSS-REFERENCE TO RELATED APPLICATION

This application is a continuation-in-part of co-pending application Ser. No. 29/009100, filed Jun. 4, 1993, now U.S. Pat. No. 353,887.

FIELD OF THE INVENTION

The present invention relates to the field of surgical devices and, more specifically, to retractors preferably used in the spinal area.

BACKGROUND OF THE ART

Spinal retractors have been developed for use in spinal surgery, such laminectomies, hemi-laminectomies, spinal fusions, repair of burst fractures, and the like, to provide surgeons with greater visibility and access to the surgical site. Spinal surgical areas benefiting from the use of retractors include, for example, the cervical, lumbosacral and the thoracolumbar regions. In order to reach the spinal area the surgeon typically must cut through several tissue layers, including the skin, fat, fascia and muscle, prior to reaching the vertebrae. The musculature in the lumbar area can be extremely resilient, requiring a great degree of force in order to retract the muscle; indeed, force on the order of 1200 pounds may be necessary to retract certain lumbosacral regions.

Retractor systems have been developed employing an assembly of blades, arms and a rack and pinion mechanism to position, spread and hold the tissue surrounding the spinal site. Typically, the blade portion is flat with straight sides, a set of teeth at the distal end for grabbing muscle, and is mounted at the proximal end to the arm by way of an aperture of some type that attaches transversely to the arm. In use, the blades are inserted into the surgical area and then attached to the arms of the rack and pinion mechanism. After positioning, the mechanism is cranked to spread the arms and retract the area, providing increased visibility and access to the surgical site.

DISCUSSION OF THE PRIOR ART

Several United States patents have issued for retractor inventions, including U.S. Pat. No. 4,747,394 issued to Watanabe; U.S. Pat. No. 4,932,395 issued to Mehdizadeh; and, U.S. Pat. No. 5,052,373 issued to Michelson. Watanabe shows a spinal retractor having a blade with straight parallel sides and a set of teeth at the distal end. The opening is rigidly integral with the blade for attachment to the arm. The toothed blade can stretch, rip or tear muscle potentially causing trauma and damage to the patient. Retracted muscle tissue can slip off straight sides of the blade during surgery requiring repositioning and extending the time of surgery, again, causing muscle trauma. Conventional straight side blade designs also compress the vascular foramen, cutting off circulation and leading to muscle narcosis and damage. Moreover, conventional straight side blade designs are not conducive to providing optimal unobstructed access to the surgical site, potentially resulting in a larger skin opening, skin tearing and unnecessary scarring. While Watanabe does disclose a bent blade design, the sides are still straight and the end of the blade still has the damaging teeth as the primary means for maintaining the retracted muscle.

Michelson discloses a straight blade design with teeth. The blade has a "C" shaped opening for attachment to the arm. This type of opening is less stable when subjected to the forces necessary to retract the muscle and can cause the blade to pop off the arm, resulting in a necessary repositioning and muscle trauma. Implantation of pins or screws into the spinal area frequently requires insertion into the surgical site of drills, driver and objects at an angle. Current retractors to not adequately permit retraction to access these angles without necessitating a larger opening, leading to a larger scar or increased potential complications. It would be desirable for a retractor to retract tissue to provide a suitably sized opening to permit implantation while gently holding the muscle. Such a retractor would not tear the tissue and would have a reduced tendency to permit the muscle to slip off during retraction.

SUMMARY OF THE INVENTION

The present invention provides in a preferred embodiment a retractor blade having a curved surface and a set of notches on both sides of the blade. The blade has a portion containing a bore. A blade holder assembly, which mounts onto a conventional rack and pinion arm, has a bushing, to which is connected an L-shaped arm. A pin extends from the distal end of the arm. The blade can be mounted on the pin in a pivotable manner. The blade is releasably maintained on the pin by a locking clip pivotably attached at one end to the blade holder assembly and at the other end terminating in a hook, which is releasably engagable with the terminus portion of the pin. The blade is maintained on the pin between the holder arm and the clip. A threaded screw having a finger knob at one end extends through a matably threaded aperture in the distal portion of the blade holder assembly. When a blade is mounted on the holder assembly and locked in, the screw terminus engages the end of the blade. The angle of the blade with respect to the blade holder assembly can be changed by turning the screw, which can apply a force to the end of the blade, pivoting the blade around the pin.

A number of alternative embodiments are described presenting different configurations and structures for blades and associated assemblies.

The curvature and notched construction of the blade reduces trauma to muscle and other tissue during retraction and retains the tissue in a more stable manner. The quick release mechanism permits rapid removal and reinsertion of different blade sizes and shapes, depending on the particular patient and musculature.

Accordingly, it is a principal object of the present invention to provide a retractor system that will reduce trauma to muscle and other tissue.

It is another object of the present invention to provide a retractor system that will reduce the size of the entry wound and reduce subsequent scarring.

It is another object of the present invention to provide a retractor system that will pivot to permit greater access to the surgical site.

It is another object of the present invention to provide a retractor system that incorporates a curved blade design which provides greater angle for insertion of pins, screws and the like.

It is another object of the present invention to provide a retractor system having a quick release mechanism for the blade, permitting rapid removal and replacement of different blades.

It is another object of the present invention to provide a retractor system having a curved blade design incorporating a pivoting blade which, when placed in the sacroilear area, will, when retraction is engaged, pivot away from and reduce the likelihood of damage to the ileac crest.

Other objects, features, and advantages of the present invention will become apparent upon reading the following detailed description of embodiments of the invention, when taken in conjunction with the accompanying drawing and the appended claims.

BRIEF DESCRIPTION OF THE DRAWINGS

The invention is illustrated in the drawings in which like reference characters designate the same or similar parts throughout the figures of which:

FIG. 1 is a top plan view of a surgical retractor system shown in situ in a preferred embodiment of the present invention.

FIG. 2 is a perspective view of a retractor blade in a preferred embodiment of the present invention.

FIG. 3 is side elevational view of the retractor blade.

FIG. 4 is top plan view of the retractor blade.

FIG. 5 is top view of a blade and blade holder in a preferred embodiment of the present invention.

FIG. 6 is side elevational view of a blade and blade holder of the present invention showing two pivot positions of the retractor blade, one of which is shown in phantom.

FIG. 7 is a side elevational cutaway view showing the retractor blade in situ with the spine and tissue layers retracted.

FIG. 8 is an alternative embodiment of the blade using a straight blade design.

FIG. 9 is another alternative embodiment of the blade using an open curved blade design.

FIG. 10 is a top view of a dynamic action pivoting blade designed for use in the lumbosacral junction.

FIG. 11 is a side view of a dynamic action pivoting blade designed for use in the lumbosacral junction.

FIG. 12 is a front view of a dynamic action pivoting blade designed for use in the lumbosacral junction.

FIG. 13 is a top plan view of a surgical retractor system shown in situ with the dynamic action pivoting blade designed for use in the lumbosacral junction.

DESCRIPTION OF THE PREFERRED EMBODIMENTS

FIG. 1 shows a surgical retractor system 10 in situ according to a preferred embodiment of the present invention, generally comprising a blade 12, a blade holder assembly 14, retractor arm 16, and a rack and pinion 18 mechanism. The system 10 is shown in situ in a top view where the vertebrae 20 are exposed and the skin 22 is retracted, exposing the vertebrae 20.

The components of the system 10 are preferably made of surgical grade steel. Alternatively, some or all of the components (such as the blade 12 or blade holder assembly 14) can be made of plastic, polymeric or composite materials, or even radiolucent materials, i.e., transparent to X-rays. For the purposes of this disclosure, the term steel will be discussed as illustrative of the material, but is intended to include other suitable materials.

FIGS. 2–4 show perspective, side and top views of the retractor blade 12 in a preferred embodiment of the present invention, which is optimally used in a lumbosacral procedure, hence it occasionally shall be referred to as a lumbosacral blade. The blade 12 has a first section 24 with an angled back portion containing a bore 26 and a planar face 27. A second section 28 extends from the first section 24 and has a distal portion 30 that is wider in width than its proximal portion 32 (with respect to the first section 24), the purpose of which will be discussed in detail below. A third section 36 extends from the distal portion 30 of the second section 28 and, similarly, has a distal portion 38 that is wider in width than its proximal portion 40. The proximal portion 40 of the third section 36 is narrower than the distal portion 30 of the second section 28. The differences in width form a notch 41 on both sides of the blade 12. The third section 36 is inched outward at an angle A with respect to the second and first sections 28 and 24 (see FIG. 3). The purpose of the inclination will be discussed in detail below, but, suffice it to say, the cupped shape of the blade 12 provides improved retraction of skin, fascia and muscle with reduced incidence of damage to tissue. A fourth section 42 extends from the distal portion 30 of the third section 36 and, similarly, has a distal portion 44 that is wider in width than its proximal portion 46. The fourth section 42 is inclined outward at an angle B with respect to the third section 36. The edges 48 are curved inward, as shown in FIG. 2. A fifth section 50 extends from the distal portion 44 of the fourth section 42 and, similarly, has a distal portion 52 that is wider in width than its proximal portion 54. The fifth section 50 is inclined outward at an angle C with respect to the fourth section 42.

The angle of inclination between the sections can vary. In a preferred embodiment, the angle A formed between the second and third sections 28 and 36, is approximately 45°, the angle B between the third and fourth sections 36 and 42, is approximately 35°, and the angle B between the fourth and fifth sections 42 and 50, is approximately 38°.

FIGS. 5 and 6 show the blade holder assembly 14 in top and side elevational view, respectively. The blade holder assembly 14 has a bushing 60, rectangular-shaped cross section, and has an aperture 62 sized to slidingly receive the arm 16. The bushing 60 is associated with an L-shaped holder arm 64 having a proximal portion 66 and distal portion 68. A pin 70 extends from the distal portion 68, generally parallel to the axis of the bushing 60. The pin 70 diameter is sized to be capable of slidingly mating with the bore 26 in the blade 12. The junction of the pin 70 and the holder arm 64 forms a stop for the blade 12.

A locking clip 72 is positioned at the distal portion 68 of the holder arm 64. The clip 72 has a hook 74 at one end and contains a bore 76 at the other end. The clip 72 is inset in a notch 78 in the holder arm 64 and pivotably maintained by a clip pin 79 passing through the bore 76. The clip hook 74 is capable of pivoting on the axis of the bore 76 and removably engaging the pin 70. In this manner, when a blade 12 is slid onto the pin 70, the hook is 74 pivoted to engage the pin 70, thereby locking the blade 12 onto the holder arm 64 and preventing its unintentional removal. The features and advantages of this quick release mechanism are discussed further hereinbelow.

The holder arm contains a threaded bore between the stop and the terminus of the holder pin 70 and is sized to receive a matingly threaded screw 80, which has a finger knob 82 at one end and a terminus 84 at the other end. The screw 80 can be adjustably threaded in and out of the holder arm 64. When a blade 12 is mounted on the holder pin 70 the back face 29 of the blade 12 is in contact with the terminus 84 of the screw 80, as shown in FIG. 6. When the screw 80 is moved away from the blade the blade pivots on the pin 70, as shown in phantom in FIG. 6.

FIG. 1 shows a rack and pinion assembly 18 generally known in the art. A pair of toothed racks 90, which extend parallel to one another, with each rack 90 being pivotably attached to an arm 16. The racks 90 are engaged by a pinion 92 mounted in a casing and which is turned by a handle (not shown) when the handle is placed in a socket in the pinion. As the pinion 92 is turned by the handle, the arms 16 are caused to move either toward or away from one another while maintaining a spaced and parallel relationship.

The each arm 16 slidingly receives the bushing 60 of at least one holder assembly 14. A pair of holder arm assemblies 14 are made in mirror image so that when a pair is mounted on each retractor arm 16, the holder arm 64 is positioned proximal, i.e., between the two retractor arms 16, as shown in FIG. 1.

The use of the present invention will now be described with respect to spinal surgery, however it is to be understood that it can be adapted for use in other procedures. A typical procedure in which the present apparatus with the lumbosacral blade 12 is used is an L5-S1 laminectomy, or similar procedure. In practice, the physician will prepare the patient in a prone position. Initial incisions are made in the skin 22 and the fascia in the lower back area to expose the muscle layer. The muscle layer is cut to expose the transverse processes. The muscle must be released from the facet joint to the tip of the processes by delicately cutting the muscle away from the bone in order to expose the vertebrae. During this step the muscle around the spinal area must be retracted to provide and maintain adequate exposure to the processes. The blade 12 can be inserted after release has reached the facet joints. The rack and pinion assembly 18 is commonly laid on the patient's back and the retractor arms 16 positioned on either side of the surgical site. A pair of blades 12 is inserted on opposite sides of the spine so that the blade 12 descends into the surgical site at approximately a 45° angle, positioning the third section of the blade vertically (parallel to the spines process). The holder arm pin 70 is inserted into the blade bore 26 and the holder arm 64 is slid onto the arm 16 of the rack 90. Initially, the blade 12 is angled with the screw 80 at an out position, as shown in FIGS. 6 and 7 in phantom, the blade 12 being in a relatively open position. As the surgeon releases muscle from the process to the midtransverse process, the muscle must be retracted further in order to access the deeper areas. To accomplish this, the blade 12 is released by pivoting the hook 74 away from and disengaging the pin 70, and the blade 12 slid off the pin 70. The screw 80 on the holder arm 64 is turned to insert the screw 80 further into the holder arm 64. The blade 12 is replaced and locked into position. The screw 80 terminus will press against the face of the first section 24 of the blade 12, pivoting the blade 12 about the pin 70 axis in the direction of the "underside" of the holder arm 64. The pivoted blade 12, shown in solid line in FIGS. 6 and 7, cups the skin, fascia and muscle and urges it away from the vertebrae and the processes. This unique pivot action gives the surgeon unobstructed access to the surgical site (shown in FIG. 7 in a cross-sectional view) not possible with previous retractors. FIG. 7 shows a device, such as a surgical screw 95, pin or retractor, which can be inserted into a surgical site at a greater angle after pivoting (indicated for illustrative purposes only as 25°) than before pivoting (indicated for illustrative purposes only as 15°).

The quick release mechanism permits the surgeon to remove a blade 12 in seconds by unclipping the locking clip 72 and sliding the blade 12 off the pin 70 and adjusting or inserting a different blade 12 and locking it into place using the hook and pin. The ease of blade replacement is significant in reducing the overall operation time, thus reducing the possibility of complications arising from protracted surgery time.

As the blade 12 retracts, the unique shape of the edges and the curve gently cup the tissue layers. The narrower portion of the second section 28 (toward the first section) does not pull the skin away as does previous retractors and therefore does not require as large an opening, resulting in a smaller and less noticeable scar. The third 36 section retracts predominantly the fascia layer. The fourth and fifth sections 42 and 50 retract predominantly the muscle layer. The muscle is allowed to curve around the notches 41 and the curved blade 12, which reduces the likelihood of the muscle popping off the blade 12.

A number of alternative embodiments are shown in FIGS. 8–13, which represent other configurations for the blade. Each of these alternative blades can be used with the pivot and release system of the present invention. FIG. 8 shows a planar blade 100 design incorporating the pivot bore and the notched edges.

FIG. 9 shows another embodiment of the blade design wherein the blade 200 is curved according to the preferred embodiment, but is of an open design. The blade 200 is composed of a first section 202, similar to the first section of the blade of the preferred embodiment. Integral with the first section 200 are a pair of rods 204 and 206 extending transversely from the first section 202 and generally parallel to each other. The rods 204 and 206 are bent to cup the muscle. The angles of inclination are generally equivalent to the angle of the blade discussed in the preferred embodiment. The rods 204 and 206 terminate at a generally rectangular plate 208. This blade 200 may be used when greater access is desired to the surgical site.

FIGS. 10–12 show a dynamic action pivoting blade assembly 300 designed for retraction in the lumbosacral junction. FIG. 11 shows a side view of the curved blade design in which the blade 302 has a flat first portion 304 having an aperture 306 defined therein; a second portion 308 inclined inward; a third portion 310 inclined inward with respect to the second portion 308; a fourth portion 312 inclined inward with respect to the third portion 310; and, a fifth portion 314 inclined inward with respect to the fourth portion 312.

FIG. 12 shows a front view with a left edge 316 of the blade 312 being straight. With respect to the straight left edge 316, the right edge 318 is angled outward at the second portion edge 320; parallel at the third portion edge 322; inward at the fourth portion edge 324; and, slightly inward at the fifth portion edge 326. The blade curvature as shown in FIG. 11 is similar to the blade curvature shown in FIG. 3, discussed above. It is to be understood that different angles can be utilized in the blade design 302 and are contemplated in the present invention.

A rectangular bushing 320 is integral with a rigid arm 332. The arm 332 comprises a rectangular top portion 334 and bottom portion 336 parallel to each other and attached to the bushing 330. A pin 338 (shown in phantom in FIG. 13) passes vertically through the arm 332 and pivotably connects the first portion 304 of the blade 302 to the arm 332.

This blade assembly 302 greatly improves exposure of the L4-L5-S1 region. This blade 302 requires a smaller skin incision than previously required and exposes the L4-L5-S1 area for canal work and instrumentation. The blade 302 works by employing the natural forces found in the region. As resistance increases during retraction when the blade 302 meets the iliac crests and begins to retract the mass in the lumbar region (see FIG. 13), maintaining S-1 exposure and gaining L4-L5 exposure. The angled portions of the right edge of the blade are contoured to give clearance to the ileac crest. While other retractors can require the surgeon to cut away bone in order to position and reposition the retractors, this embodiment of the present invention permits the retractor to be used without damaging bone and better maintaining the natural integrity of the area. This design also reduces the danger of splitting the ileac crest, which can occur with non-pivotable retractor blades. This design is particularly useful with patients who have scoliosis, because the blades 302, which are mirror images when mounted on the rack and pinion mechanism, move independently from one another where the spine is not axially positioned.

While the invention has been described in connection with certain preferred embodiments, it is not intended to limit the scope of the invention to the particular forms set forth, but, on the contrary, it is intended to cover such alternatives, modifications, and equivalents as may be included within the spirit and scope of the invention as defined by the appended claims.

We claim:

1. A pivotable surgical retractor blade assembly, comprising:

an enclosed bushing having a bore defined therein;

upper and lower plates extending transversely from said bushing;

a pin extending between said upper and lower plates;

a retractor blade comprising a first section having distal and proximal portions and containing an aperture therein and pivotably mounted between said upper and lower plates such that said blade can pivot only in a horizontal plane, a second section having distal and proximal portions and extending from the distal portion of said first section such that said second section is angled downward from said first section at an angle of less than 90° from the horizontal, a third section having distal and proximal portions and extending from the distal portion of said second section such that said third section is angled downward from said second section at an angle of less than 90° from the horizontal, a fourth section having distal and proximal portions and extending from the distal portion of said third section such that said fourth section is angled downward from said third section at an angle of less than 90° from the horizontal, a fifth section having distal and proximal portions and extending from the distal portion of said fourth section such that said fifth section is angled downward from said fourth section at an angle of less than 90° from the horizontal, each of said first, second, third, fourth and fifth sections having a left and a right edge whereby said left edges are co-linear and whereby said first section right edge is substantially parallel with said first section left edge and has a first predetermined width, said second section right edge is angled outward to said third section right edge which is substantially parallel with said third section left edge and has a second predetermined width larger than said first predetermined width, and said fourth section right edge is angled inward from said third section right edge to a third predetermined width smaller that said second predetermined width.

* * * * *